United States Patent [19]

Radziemski et al.

[11] Patent Number: 4,561,777

[45] Date of Patent: Dec. 31, 1985

[54] APPARATUS AND METHOD FOR QUANTITATIVE DETERMINATION OF MATERIALS CONTAINED IN FLUIDS

[75] Inventors: Leon J. Radziemski; David A. Cremers, both of Los Alamos, N. Mex.

[73] Assignee: The United States of America as represented by the United States Department of Energy, Washington, D.C.

[21] Appl. No.: 415,515

[22] Filed: Sep. 7, 1982

[51] Int. Cl.[4] .............................. G01N 21/63
[52] U.S. Cl. ....................... 356/318; 356/38
[58] Field of Search ............... 356/36, 38, 317, 318, 356/417

[56] References Cited

U.S. PATENT DOCUMENTS 2,076,544  4/1937  Drinker et al. ............... 356/38
3,088,364  5/1963  Rozsa et al. .................. 356/38

FOREIGN PATENT DOCUMENTS 100323  6/1982  Japan ........................ 356/318

OTHER PUBLICATIONS

Ozaki et al., *Tetsu To Hagane*, vol. 68, No. 7, 1982, pp. 863–871.
Rozsa et al., *Applied Spectroscopy*, vol. 19, No. 7, 1965, pp. 7–10.
Scott et al., *Spectrochimica Acta* 26B, 1971, pp. 707–719.
Treytl et al., *Applied Spectroscopy*, vol. 25, No. 3, 1971, pp. 376–378.
Treytl et al., *Analytical Chemistry*, vol. 47, No. 8, Jul. 1975, pp. 1275–1279.
Piepmeier et al., *Analytical Chemistry*, vol. 41, No. 6, May 1969, pp. 700–707.
Treytl et al., *Analytical Chemistry*, vol. 43, No. 11, Sep. 1971, 1452–1456.
Marich et al., *Journal of Physics* E 7, 1974, pp. 830–834.
Ozaki et al., *Tetsu to Hagane*, vol. 68, No. 7, 1982, pp. 872–880.
Watson et al., *J. Phys. E.*, vol. 10, No. 12, Dec. 1977, pp. 1227–1228.

*Primary Examiner*—F. L. Evans
*Attorney, Agent, or Firm*—Samuel M. Freund; Paul D. Gaetjens; Judson R. Hightower

[57] ABSTRACT

Apparatus and method for near real-time in-situ monitoring of particulates and vapors contained in fluids. Initial filtration of a known volume of the fluid sample is combined with laser-induced dielectric breakdown spectroscopy of the filter employed to obtain qualitative and quantitative information with high sensitivity. Application of the invention to monitoring of beryllium, beryllium oxide, or other beryllium-alloy dusts is demonstrated. Significant shortening of analysis time is achieved from those of the usual chemical techniques of analysis.

17 Claims, 5 Drawing Figures

APPARATUS AND METHOD FOR QUANTITATIVE DETERMINATION OF MATERIALS CONTAINED IN FLUIDS

This invention is the result of a contract with the Department of Energy (Contract No. W-7405-ENG-36).

BACKGROUND OF THE INVENTION

The present invention relates generally to the quantitative determination of materials contained in fluids, and more particularly to the quantitative analysis of materials contained in fluids using in combination the laser-induced dielectric breakdown spectroscopy technique with a filtration system which traps the material under investigation from the fluid sample (gases, liquids or combinations), thereby concentrating it and improving the limit of detection for this material.

It is known that many vapors and particulates are harmful to humans if inhaled. It is therefore necessary to achieve as close to real-time monitoring of ambient environments for the presence of metallic compounds and other dusts as is possible in order to warn workers involved in fabrication operations, metal processing, mining, etc., of substantial concentrations of harmful material disposed such that there is a significant possibility of bodily intake. For example, beryllium, beryllium oxide, or other beryllium-alloy dusts are especially harmful and occur frequently in the nuclear industry.

Beryllium dust is usually monitored by filtration of contaminated air with subsequent chemical processing of the contaminated filter material followed by atomic absorption spectrochemical analysis of the resulting solution. The beryllium mass so determined is divided by the volume of air passed through the filter to obtain an average concentration. The procedure is time-consuming, requires an analytical laboratory and skilled analytical chemists, and is far from being a real-time monitoring technique.

The apparatus and method of the present invention are based on a combination of the filtration technique mentioned hereinabove and laser-induced dielectric breakdown spectroscopy for quantitative analysis of surfaces or material on surfaces. Light from the breakdown induced on the surface of the impregnated filter is collected, dispersed, time-resolved, and recorded, enabling quantitative analysis of the collected material once the apparatus has been calibrated. The rapid analysis of the filter brings the overall analytical technique much closer to a real-time procedure.

U.S. patent application Ser. No. 342,681, "Method For Spectrochemical Analysis Using Time-Resolved Laser-Induced Breakdown," filed Jan. 26, 1982, is assigned to the same party as the instant invention (U.S. Department of Energy), and discloses the laser-induced dielectric breakdown spectrochemical analysis technique. Thomas R. Loree and Leon J. Radziemski comprise the inventive entity of the earlier application. The present invention is an improvement thereon in that for very low impurity concentrations in the fluid under investigation, the dielectric breakdown spectrochemical analytical procedure by itself has insufficient sensitivity to be of value. However, if the impurity is first concentrated by use of appropriate filters, a concept not disclosed in Loree et al., and the filters then quantitatively analyzed by the aforementioned spectrochemical analytical technique, improved detection limits can be obtained for the combination. Moreover, although the present invention does not quite allow real-time monitoring, it is considerably faster than the previously used wet-chemical spectroscopic technique.

SUMMARY OF THE INVENTION

An object of the instant invention is the quantitative monitoring of the concentration of materials contained in fluid samples.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention includes a filter of known collection efficiency through which a known volume of the sample of fluid has been passed, means for inducing dielectric breakdown on a portion of the surface of this filter, and means for quantitatively detecting, and recording the emitted light. Preferably, means are provided for spectrally resolving the light emitted from the dielectric breakdown since such light includes spectral features characteristic of the captured material which is to be quantitatively analyzed for, and simultaneously, features characteristic of the filter material itself. Depending on the material under investigation, it may further be desirable to observe the emitted light within a particular time period after the onset of dielectric breakdown. It is also preferred that means are provided for collecting and concentrating the emitted light before this light enters the resolving means. In the situation where the impurity material is in very low concentrations, means are provided for averaging a plurality of quantitatively detected, temporally and spectrally resolved emitted light signals until a useful signal-to-noise ratio is obtained. Preferably, the dielectric breakdown inducing means includes repetitively pulsed, high intensity laser radiation focused onto the filter material surface portion. Preferably also, means are included for changing the portion of the filter surface undergoing dielectric breakdown and sampling a plurality of locations on this surface. The purpose is to reduce the scatter in the quantitatively detected emitted light signals due to both local irregularities in trapping efficiency of the filter material for the material under investigation and the statistical nature of the location of particle impact at low material densities. Further, along these lines, preferably means are provided to increase the area of the filter surface portion undergoing dielectric breakdown at one time.

In the further aspect of the present invention, in accordance with its objects and purposes, the method hereof may also include flowing a known volume of a fluid sample through filter material selected to collect the material under investigation with known efficiency, causing dielectric breakdown to occur over a portion of the surface of this filter material from which electromagnetic radiation which include molecular emissions and ionic and neutral atomic spectral features characteristic of the elemental species present on the filter material surface portion, characteristic of filter material, and characteristic of the fluid, is emitted; resolving individual spectral features from this emitted radiation in order to separate emissions characteristic of the material under investigation; quantitatively detecting and recording these resolved characteristic spectral features; calibrating the procedure by using known material contamination levels on the filter material and repeating the dielectric breakdown, collecting, resolving, quantitatively detecting and recording steps; and comparing the recorded signals from both the sample under investigation and the calibration procedure to determine the impurity material concentration. It is preferred that the filter is first removed from contact with the fluid sample before the dielectric breakdown is caused to occur in order to reduce spectral interferences due to the fluid. In cases where the emitted spectrum detection is "blinded" by an initially intense continuum background emission or cluttered by a significant number of rapidly dying ionic emission spectral features temporally late features due to molecular emissions, a specific time period is chosen after the spark formation before the detection step is performed in order to discriminate against these unwanted emissions, which either die away faster or become apparent after emission from the excited neutral atoms, thereby increasing the signal-to-noise ratio either for the neutral atomic signals or for long-lived ionic signals, as in the case of beryllium. It is further preferred that the emitted electromagnetic radiation from the dielectric breakdown be collected and concentrated before spectral resolution into its constituent components. It is also preferred that several filter portions are analyzed to avoid local irregularities in filter collection efficiency giving rise to erroneous concentration measurements. Preferably, in cases where the impurity material is in low concentration, or its characteristic spectral features are weak because of spectroscopic or detection reasons, a plurality of light signals from repeated dielectric breakdowns of the filter material surface are averaged to improve the signal-to-noise ratio. Finally, it is preferred that the dielectric breakdown be induced using pulsed, high intensity laser radiation focused onto a portion of the contaminated filter. The method of the subject invention is an general procedure and greatly expedites the identification and determination of suspended particulate concentration in the ambient air in laboratory, mining, and milling environments. In particular, the present invention cuts precious time off of the usual beryllium dust monitoring procedure, time which can reduce the danger of inhalation of this dangerous material. In addition, near real-time detection can be achieved at beryllium levels significantly below that which have been considered to be harmful.

BRIEF DESCRIPTION OF THE DRAWINGS

The accompanying drawings, which are incorporated in and form a part of the specification, illustrate one embodiment of the present invention and, together with the description, serves to explain the principles of the invention. In the drawings.

DETAILED DESCRIPTION OF THE INVENTION

Figure 1:
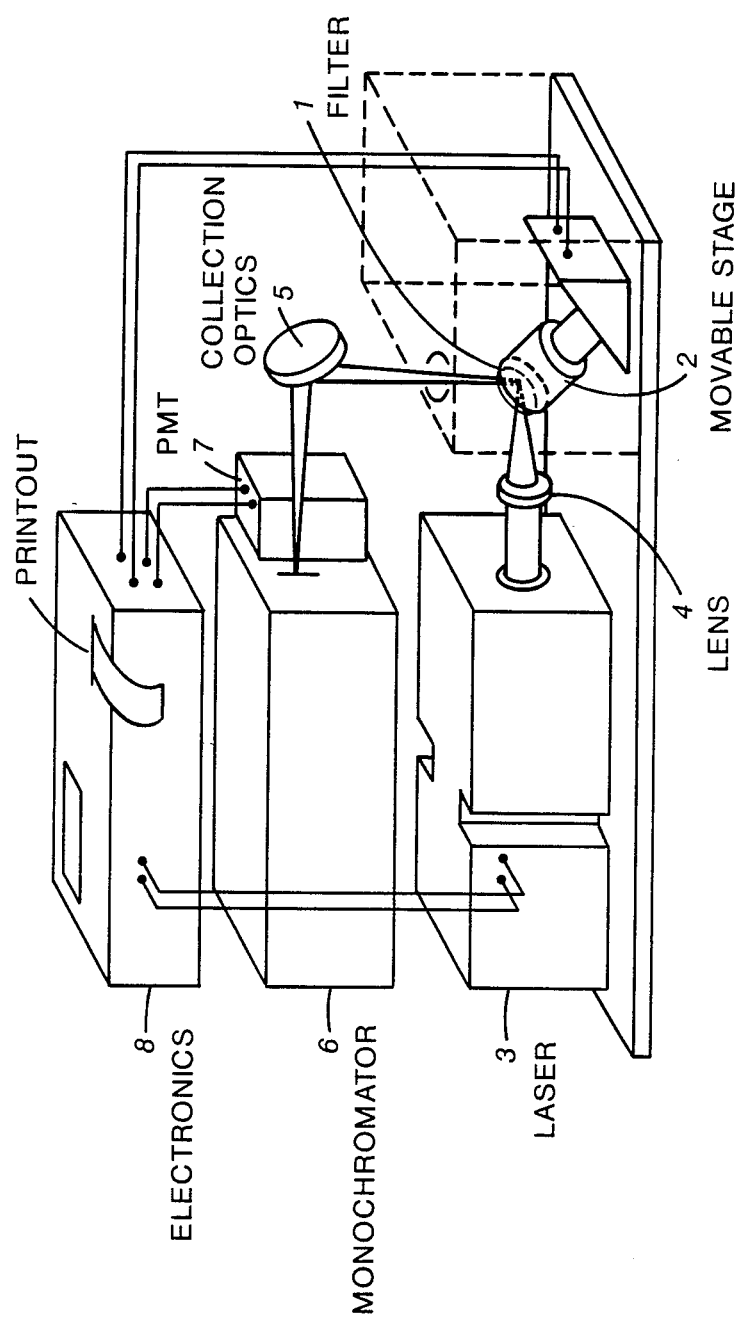
FIG. 1 is a schematic representation of the apparatus for the analysis of previously contaminated filters utilizing laser-induced dielectric breakdown with subsequent quantitative spectroscopic analysis of the emitted light.

Turning now to the drawings, initially to FIG. 1, a schematic representation of the apparatus utilized in the preferred embodiment of the instant invention is shown. A known volume of the fluid under investigation is filtered through filter material of known collection efficiency for the suspected impurity. The contaminated filter 1 is then removed from the fluid and placed on a stage 2. Light from an intense, pulsed laser 3 is focused by a lens 4 onto the surface of the filter causing dielectric breakdown over a particular surface portion. The stage 2 is movable to allow several different portions of the filter to be investigated, thereby avoiding incorrect results due to spatial irregularities in filter trapping efficiency. It is likewise advantageous to use a cylindrical lens 4 for the focusing so that a substantial filter surface area is caused to break down at one time under the influence of the laser light. Light is emitted from the breakdown process which comprises a background continuum, spectral features from excited molecules formed as a result of recombination of atoms, spectral features from excited ions, and spectral features from excited neutral atomic species, the latter two emissions being characteristic of the elemental species present. In general, improved signal-to-noise ratio for the atomic spectral features can be obtained by waiting for the continuum emission to die down before detection of the radiation is commenced. If the spectrum is cluttered in the region of interest for the impurity material, an additional wait will generally cause the ionic spectrum to disappear leaving principally the neutral atomic features. The continuum and the ionic spectral features are in general known to have a shorter lifetime than the emissions from the excited neutral atomic species. It should be pointed out that for some elements (Be, for example) some ionic emissions are long-lived and provide a more sensitive indicator than neutral atomic emissions. Reduction in spectral clutter is one reason the filter material is removed from the presence of the fluid under investigation. The light collection and concentration optics 5 gather as much of the emitted radiation as is necessary for obtaining reasonable sensitivity from the apparatus, and focus this light into a monochromator 6 which resolves the spectral features. A photomultiplier tube 7 and appropriate electronics 8 quantitatively detect the intensities and wavelengths of the breakdown spectrum enabling qualitative and quantitative analysis of the filter surface. A calibration of the apparatus with particular filters whereon known quantities of the material(s) of interest are deposited is necessary to achieve the quantitative analysis. In the event of small impurity concentration on the filter under investigation, repeated light intensity measurements from individual dielectric breakdown events are averaged to improve the signal-to-noise ratio of detection.

Figure 2:
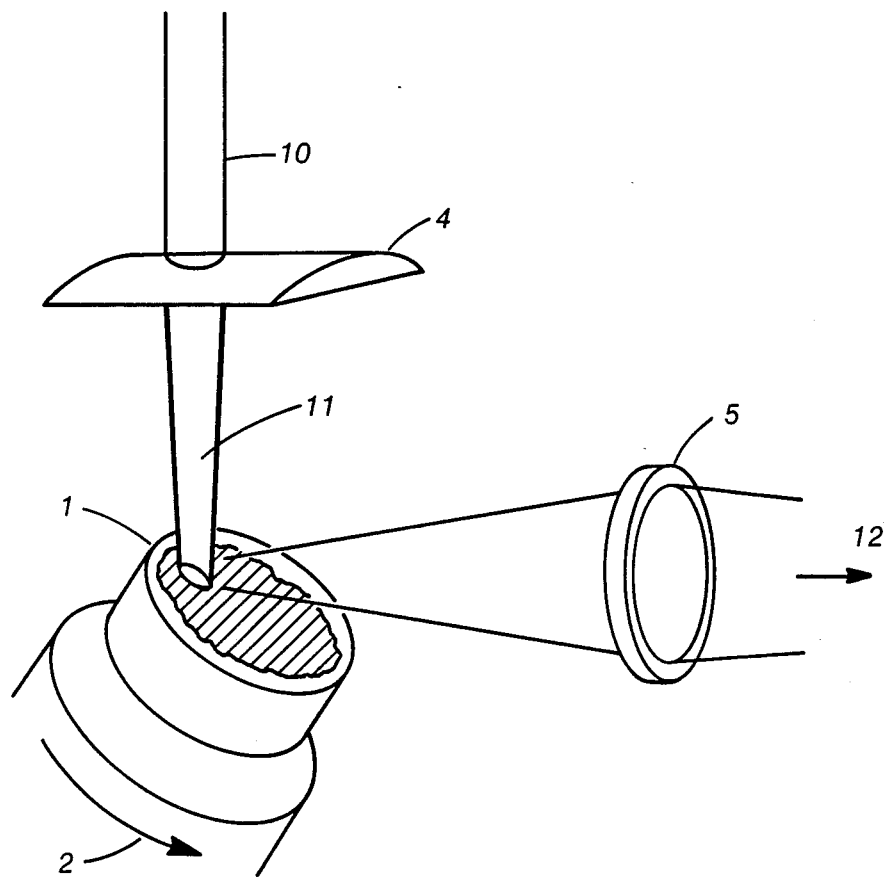
FIG. 2 shows an embodiment of the filter interrogation apparatus including the laser focusing and emitted light collecting optics.

FIG. 2 shows the spark formation and filter irradiation in greater detail. Laser light 10 is focused by a cylindrical lens 4 onto the filter 1 surface to produce dielectric breakdown. The purpose of using a cylindrical lens is to produce a large, elliptically shaped sampling region on the filter surface. This enables the entire surface to be investigated through repeated breakdown formation without a significant number of gaps and in a shorter period of time. That is, by beginning at the filter center and in steps moving the breakdown region out along a radius while at the same time rotating the filter about its central axis, one can cover successively larger annular regions until the entire filter surface has been covered. This procedure is very important since for low particle density analyses one cannot locate in advance where a given dust particle will be trapped on the filter surface. A sampling procedure which resulted in unexamined surface regions would give rise to inaccurate results. The instant procedure also compensates for non-uniformities in filter trapping efficiency.

Figure 3:
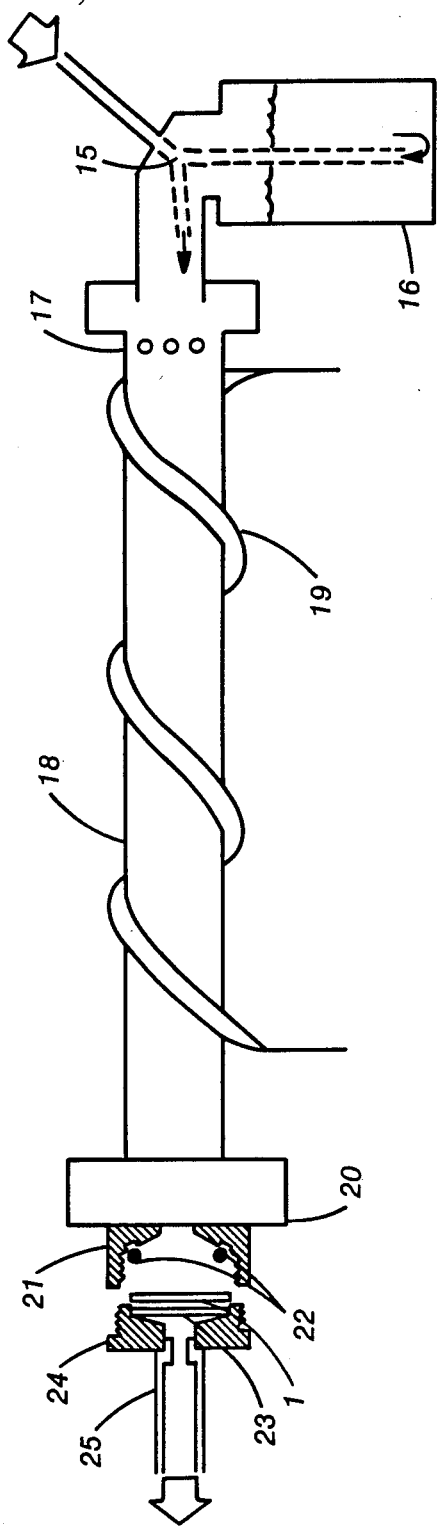
FIG. 3 is a schematic representation of the contaminant deposition (nebulizer/heat-pipe/filter holder) apparatus for calibration purposes.

FIG. 3 shows a schematic representation of the nebulizer apparatus utilized to deposit known amounts of beryllium on filter surfaces. This procedure is important to the calibration of the overall analytical system (filter plus dielectric breakdown spectroscopy apparatus). A removable cup 16 is partially filled with a solution of a beryllium salt. A venturi tube 15 is used to nebulize this solution down the bore of a heated pipe 18. The venturi is operated from a pressurized air supply. A combination of an exit tube 25 held at a reduced pressure, and orifices 17 permit the reduction in pressure at the pipe orifice of the venturi tube which draws the nebulized solution down the pipe 18 toward the filter 1. The pipe 18 is wrapped with heating tape 19 which heats the pipe to desolvate the droplets of the aspirated solution producing particulates which deposit on the filter surface. It is known that direct liquid deposition does not produce reliable calibrations. From the decrease in fluid level in the cup and the determinable transport efficiency of the nebulizer/heat-pipe apparatus, and the fact that a known amount of the salt incident on the filter 1 is trapped on its surface, a known quantity of beryllium is deposited on the filter. The trapping efficiency is determined experimentally and is related to the particular choice of filter material (0.8 $\mu$m pore cellulose acetate is commonly used for beryllium analyses). The filter is then removed from the demountable housing 21, 22, 23, and 24 which is attached to a flange 20 on the end of the heated pipe 18 and placed on the movable stage 2 shown in FIGS. 1 and 2.

Figure 4:
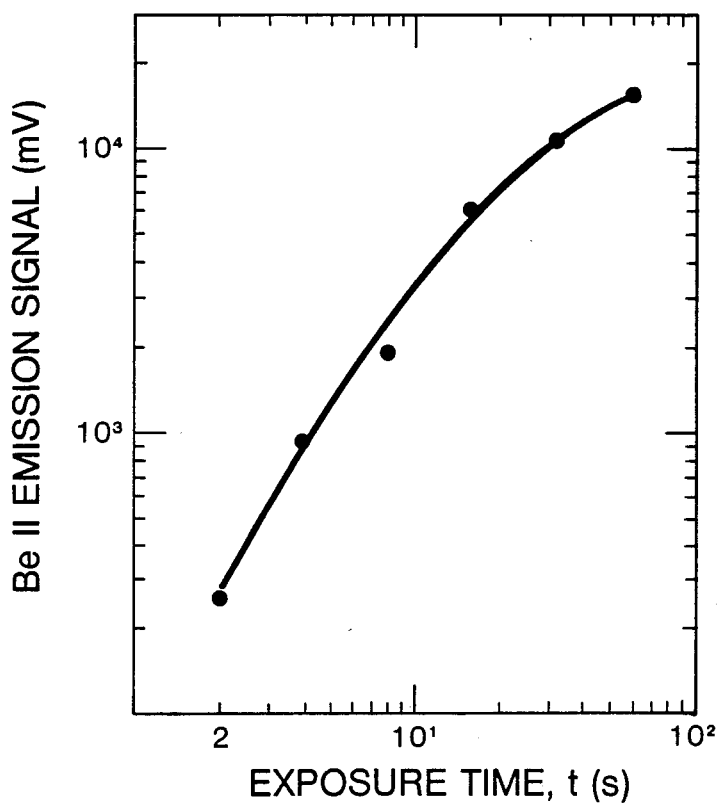
FIG. 4 is a calibration curve for the instant apparatus for the detection of beryllium particulates.

FIG. 4 is a calibration curve showing the observed beryllium light emission signal as a function of the exposure time of the filter to the particulates in the calibration apparatus. The 313.1 nm Be II doublet spectroscopic feature was monitored. Although the abscissa reads in units of time of filter exposure in the calibration apparatus, this can be related to Be mass on a particular filter since the mass deposited is proportional to the time exposed to the Be salt particulates. The curvature displayed at the higher deposition quantities (longer exposure times) may be due to incomplete vaporization of the collected material by the laser pulses in the breakdown process.

Figure 5:
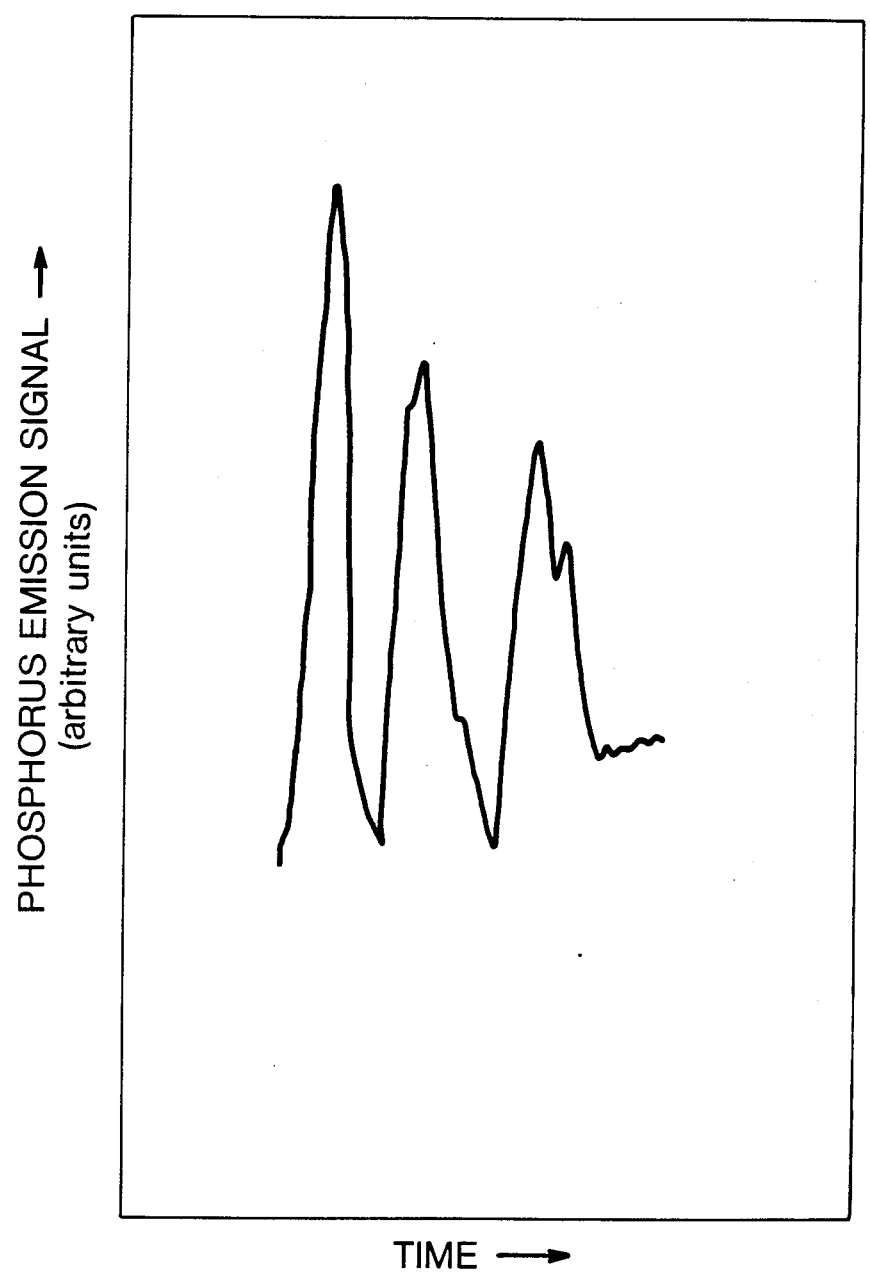
FIG. 5 shows the phosphorus signal obtained from repetitive scans of filter portions contaminated with dimethylmethylphosphonate (peaks) compared with uncontaminated portions of the same filter (valleys).

FIG. 5 shows the phosphorus emission signal (peaks) for a filter upon one-half of which dimethylmethylphosphonate is deposited. The decrease in peak signal with successive surface interrogations shows results of repeated spark formation which vaporizes a portion of the surface and deposited material, thereby reducing the material available for subsequent vaporizations. The valleys represent the interrogation of the uncontaminated one-half of the filter material and show a null reading. The phosphorous signal (from P I) was observed using 253.6 nm light emission from the dielectric breakdown of the dimethylmethylphosphonate contaminant.

Reference will now be made in detail to the present preferred embodiment of the invention, an example of which is illustrated in the accompanying drawings. Perhaps the most important of the details of the present invention is the calibration procedure which is essential to its operation. A calibration curve of the Be emission signal versus Be mass trapped on the filter surface was developed by depositing a known amount of beryllium particulates on filters and monitoring the signal from filters so prepared. Of importance in this procedure is the systematic interrogation of the entire filter surface as was described hereinabove in the discussion of FIG. 2. The sum of the signals for all of the surface portions monitored reflects the total Be mass trapped.

Table I shows the results of analysis for calibration filters with various quantities of deposited beryllium. Column I represents the exposure time of the filters to the beryllium salt particulates in the calibration apparatus, and this time is the independent variable plotted in FIG. 4. FIG. 4 contains as its ordinate the entries of Col. 3 from the Table which represent the average signal, s. The conversion from exposure time to beryllium mass deposited is 0.17 $\mu$g/s which is derived from the nebulized Be solution concentration, the solution uptake rate, the particulate transport efficiency of the nebulizer/heat-pipe apparatus, and the particulate trapping efficiency of the filter.

TABLE I

| EXPOSURE TIME(s) | NUMBER OF FILTERS | s (mV) | $\sigma$ (mV) |
|---|---|---|---|
| 2 | 16 | 253 | 32 |
| 4 | 4 | 967 | 33 |
| 8 | 4 | 1910 | 160 |
| 16 | 4 | 6150 | 500 |
| 32 | 4 | 10750 | 1130 |
| 60 | 4 | 15330 | 995 |

Column 2 shows the number of filters interrogated at each exposure time (Be mass), while Column 4 represents the standard deviation of the signals, $\sigma$. From the data one can calculate a Be mass detection limit of 0.29 s of exposure which corresponds to 50 ng of beryllium on a filter. The time required to collect this amount of Be from the ambient air assuming the current OSHA 8-hr limit concentration of 2 $\mu$g/m$^3$ and typical air flow rates of 40 L/min. through the monitoring filters is approximately 37 s. In terms of minimum detectable concentration, a concentration of $3 \times 10^{-3}$ $\mu$g/m$^3$ of beryllium in air flowed through a filter for 8 hours at 40 L/min. will result in a 50 ng Be mass deposit on the filter. This concentration is 680 times below the OSHA 8-hr average exposure limit. Finally, the generality of the present technique for measuring different materials deposited on the filter is shown by the results displayed in FIG. 5 for the organic compound dimethylmethylphosphonate.

In summary, by combining laser-induced dielectric breakdown spectroscopy with simple filtration of fluid samples, near real-time in situ monitoring of impurities can be achieved. In general, impurity levels of interest for industrial health applications are too low for direct, "true" real-time procedures. In particular, beryllium and its compounds are extremely toxic, and at acceptable industrial ambient air levels, filters must be used to collect the dust particles. The filters are then chemically analyzed to determine the concentration of pollutants which is a slow and tedious process. The present invention makes the analysis of the impregnated filters rapid and routine, thereby allowing a somewhat closer approximation to real-time monitoring. This is important since the sooner workers are informed of unacceptably high toxic substance levels, the less the danger of intake of dangerous quantities of beryllium or its compounds.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for investigating fluid samples having at least one material carried by particulates suspended therein the concentration of which material is to be monitored, said method comprising the steps of:
   a. flowing a known volume of a sample through filter material selected to collect the material under investigation on its surface with known efficiency;
   b. causing high intensity laser radiation to interact with a significant portion of the surface of the filter material which induces dielectric breakdown to occur substantially thereon from which there is emitted electromagnetic radiation which includes ionic and neutral atomic spectral features characteristic of the elemental species present on the filter material surface portion, molecular emissions, and spectrally broad background emissions;
   c. quantitatively detecting and recording the emitted radiation;
   d. calibrating said quantitatively detecting and recording step by depositing known contamination levels of the material under investigation on the filter material and repeating said steps b-c; and
   e. comparing said quantitatively detecting and recording step for the material under investigation with said calibrating step to determine the concentration of the material contained in the particulate in the fluid sample.

2. The method as described in claim 1, wherein the emitted electromagnetic radiation is spectrally resolved before said quantitatively detecting step in order to separate the emissions characteristic of the collected sample material from each other, from emissions due to other of the elemental species collected on the filter material surface, and from unwanted interfering electromagnetic radiation characteristic of the filter surface portion undergoing the dielectric breakdown and the spectrally broad background emissions.

3. The method as described in claim 2, wherein said quantitatively detecting step is performed during a specific time period after the onset of the dielectric breakdown in order that said quantitatively detecting step can be accomplished with a minimum of the unwanted interfering electromagnetic radiation.

4. The method as described in claim 3, wherein said calibrating step further comprises:
   a. preparing a solution of known concentration having the atomic species of the material under investigation dissolved therein;
   b. nebulizing the solution at a known takeup rate;
   c. dispersing the nebulized solution with a known flow of carrier gas;
   d. desolvating the dispersed nebulized solution to produce particulates therefrom; and
   e. directing the particulates onto the filter material for a known period of time, whereby the particulates are collected on the surface of the filter material.

5. The method as described in claim 4, wherein the filter material is first removed from contact with the sample fluid before the dielectric breakdown causing step is performed.

6. The method as described in claim 5, wherein the emitted electromagnetic radiation is collected and concentrated following said dielectric breakdown causing step, and before said spectrally resolving step.

7. The method as described in claim 6, wherein a plurality of the filter material surface portions are examined by performing said dielectric breakdown causing step and the steps following this step and the results therefrom added in order to minimize the effects of preferential deposition onto the filter material surface of the material under investigation at a particular location on the filter material surface, and to insure that substantially all the filter surface is investigated.

8. The method as described in claim 7, wherein the fluid sample includes gases.

9. The method as described in claim 8, wherein the gases include air, and the material carried by the suspended particulates includes beryllium, mercury, arsenic, lead and dimethylmethylphosphonate.

10. The method as described in claim 9, wherein the steps of flowing a known volume of a sample through filter material selected to collect the material under investigation with known efficiency, causing high intensity laser radiation to interact with a significant portion of the surface of the filter material which induces dielectric breakdown to occur substantially thereon from which there is emitted a electromagnetic radiation which includes ionic and neutral atomic spectral features characteristic of elemental species present on the filter material surface portion, molecular emissions, and spectrally broad background emissions, and quantitatively detecting and recording the emitted radiation, are sequentially repeated and the results therefrom averaged until statistically significant data is obtained before the step of comparing said quantitatively detecting and recording step for the material under investigation with said calibrating step to determine the concentration of the material contained in the particulate in the fluid sample is performed.

11. An apparatus for investigating fluid samples having at least one material carried by particulates suspended therein the concentration of which is to be monitored, said apparatus comprising in combination:
   a. a filter of known collection efficiency through which as been passed a known volume of a fluid sample and upon which a quantity of the material to be monitored has been collected;
   b. means for generating repetitively pulsed, high intensity laser radiation;
   c. cylindrical lens means for receiving the repetitively pulsed, high intensity laser radiation generated by said laser radiation generating means, and for focusing the laser radiation into an elongated shape having significant area on the surface of the filter material, thereby inducing dielectric breakdown to occur over a significant portion of substantially the surface of the filter material from which there is emitted electromagnetic radiation which includes ionic and neutral atomic spectral features characteristic of the elemental species present on the filter material surface portion, molecular emissions, and spectrally broad background emissions;

d. means for quantitatively detecting and recording the emitted characteristic spectral features; and e. means for calibrating the magnitude of the quantitatively detected, emitted characteristic spectral features in order to relate the magnitude thereof to the material concentration to be monitored.

12. The apparatus as described in claim 11, further comprising means for spectrally resolving the emitted characteristic spectral features in order to separate emissions characteristic of the collected sample material from each other, from emissions due to other of the elemental species collected on the filter material, and from interfering, unwanted spectrally broad background emissions and emissions characteristic of the filter surface portion undergoing the dielectric breakdown.

13. The apparatus as described in claim 12, further comprising means for collecting and concentrating the emitted characteristic spectral features and spectrally broad background emissions before they enter said spectrally resolving means.

14. The apparatus as described in claim 13, further comprising means for changing the substantially surface portion undergoing the dielectric breakdown in order to sample a plurality of locations on the filter material surface until the entirety of the surface is interrogated, to avoid erroneous concentration determinations resulting from accidental local irregularities in trapping of the material under investigation, and to insure that substantially all of the collected material is caused to undergo the dielectric breakdown.

15. The apparatus as described in claim 14, further comprising means for selecting a specific time period after the onset of the dielectric breakdown during which the detecting means can detect the spectrally resolved characteristic spectral features with a minimum of the interfering, unwanted radiation.

16. The apparatus as described in claim 15, wherein said calibrating means further comprises in combination:

a. means for quantitatively nebulizing a solution of the material the concentration of which is to be monitored;

b. means for quantitatively dispersing the nebulized solution in a known volume of a carrier gas, and desolvating the dispersed solution, thereby producing particulates suspended in the carrier gas;

c. means for directing the particulates onto the surface of a filter material in order to deposit a known mass of the material the concentration of which is to be monitored; and d. means for removably holding the filter.

17. The apparatus as described in claim 16, wherein the laser radiation contains 50–100 mJ of energy per pulse.

* * * * *